United States Patent [19]

Taheri

[11] Patent Number: 4,631,053
[45] Date of Patent: Dec. 23, 1986

[54] OXYGENATOR

[76] Inventor: Syde A. Taheri, 268 Dan Troy Dr., Williamsville, N.Y. 14221

[21] Appl. No.: 590,701

[22] Filed: Mar. 19, 1984

[51] Int. Cl.⁴ .............................................. A61M 3/00
[52] U.S. Cl. ......................................... 604/49; 604/4;
 128/DIG. 3; 261/DIG. 28
[58] Field of Search ...................... 261/DIG. 28, 122;
 604/4, 48, 147, 23–26, 52–53; 128/DIG. 3, 632,
 635; 623/1; 422/45; 128/344

[56] References Cited

U.S. PATENT DOCUMENTS

| 3,505,686 | 4/1970 | Bodell | 3/1 |
| 4,215,082 | 7/1980 | Danel | 261/122 |
| 4,265,249 | 5/1981 | Schindler et al. | 128/635 |
| 4,387,711 | 6/1983 | Merry | 128/207.15 |
| 4,583,969 | 4/1986 | Mortenser | 604/49 |

FOREIGN PATENT DOCUMENTS 1280481 11/1961 France ................................. 604/101

OTHER PUBLICATIONS

"An Implantable Artificial Lung", Bodell et al., JAMA, Jan. 25, 1965, vol. 191, No. 4, pp. 125–127.
"Insertion Instructions for Kontron Cartiovascular Percataneous Double Lumen Intra-Aortic Balloon", Kontron Medical, Dec. 15, 1982, pp. 1–13.

Primary Examiner—Stephen C. Pellegrino
Assistant Examiner—Gene B. Kartchner
Attorney, Agent, or Firm—Christel, Bean & Linihan

[57] ABSTRACT

Method and apparatus for the oxygenation of the blood. The apparatus (14) includes a hollow membrane (16) having a central tubular portion (32) and a plurality of radially outwardly extending diffusion elements (34). The membrane is disposed within a sheath (18) and both are supported by a flexible wire (20), one end of the membrane and sheath being secured to the wire. The other end of the membrane and sheath are secured to a tube (22) through which oxygen may be supplied to the hollow membrane. The sheath and membrane may be twisted upon the wire (20) to facilitate insertion and, once inserted, they may be untwisted to resume their operable position.

10 Claims, 3 Drawing Figures

OXYGENATOR

TECHNICAL FIELD

The present invention relates generally to oxygenators, and more particularly to a disposable oxygenator which may be positioned within a patient's body, as for example in the inferior vena cava, for the oxygenation of the blood.

BACKGROUND OF THE INVENTION

Blood oxygenators are well known in the art and are used in various surgical procedures for introducing oxygen into the blood. For example, during open heart surgery the patient is interconnected with an oxygenator which is disposed outside of the body of a patient, the oxygenator, which is sometimes referred to as a heart-lung machine, will cause oxygen to be introduced into the blood system. Differing forms of oxygenators are known, and one form is referred to as a membrane type wherein the blood is caused to flow to one side of a gas permeable membrane, the other side of the membrane being supplied with oxygen. Where there is sufficient pressure gradient drop between the oxygen supply and the blood, as for example four pounds per square inch, the oxygen will pass through the membrane and into the blood.

While these devices are useful for major surgical procedures, such as open heart surgery, they require close monitoring by attending personnel, are very expensive, and further require that the patient's normal circulatory system be shunted to an oxygenator disposed outside of the body. The time that such a machine can be used with a particular patient is also somewhat limited.

There are many situations where patients require oxygenation of the blood but where it is desirable that a less complex device be provided for such purposes. For example, such a device would be desirable when treating patients with cardiogenic shock, with severe pulmonary insufficiency, with hyaline membrane disease, during severe asthmatic attacks, and also post-operatively where there is a sudden pulmonary insufficiency. It is also desirable that a patient be treated with an oxygenator over a period of time which may be longer than is generally practical with conventional oxygenators.

OBJECTS AND SUMMARY OF THE INVENTION

It is an object of the present invention to provide an oxygenator which overcomes the disadvantages of known oxygenators, which oxygenator can be positioned within the circulatory system of a patient.

More particularly, it is an object of the present invention to provide a disposable oxygenator which can be easily inserted into major blood vessels of a patient, such as the inferior vena cava, for the purpose of oxygenating the blood.

Furthermore, it is an object of the present invention to provide a method for the intercaval insertion of a disposable oxygenator.

In accordance with a preferred form of this invention the system includes a hollow tubular gas permeable membrane oxygenator having numerous side branches which resemble pine needles on a pine branch, the side branches measuring approximately 1 mm in diameter. The membrane oxygenator is mounted on a support wire which holds the system stiff for insertion into the inferior vena cava or another major blood vessel. The length of the membrane oxygenator is approximately 30 to 40 cm in length and its full width is approximately 2 cm. The membrane oxygenator is mounted within a sheath, and both one end of the membrane oxygenator and a corresponding end of the sheath are secured to the support wire. The other end of the membrane oxygenator and the sheath are secured to an oxygen supply tube. The support wire can be rotated within the oxygen supply tube to cause the membrane and sheath to twist about the support wire to reduce the overall diameter to facilitate insertion into the blood vessel. The insertion of the system is percutaneously and devices are available for percutaneous insertion of the system.

The foregoing objects and other objects and advantages of this invention will become more apparent from the following detailed description taken in conjunction with the accompanying drawings in which a preferred form of this invention is illustrated.

DETAILED DESCRIPTION

Figure 1:
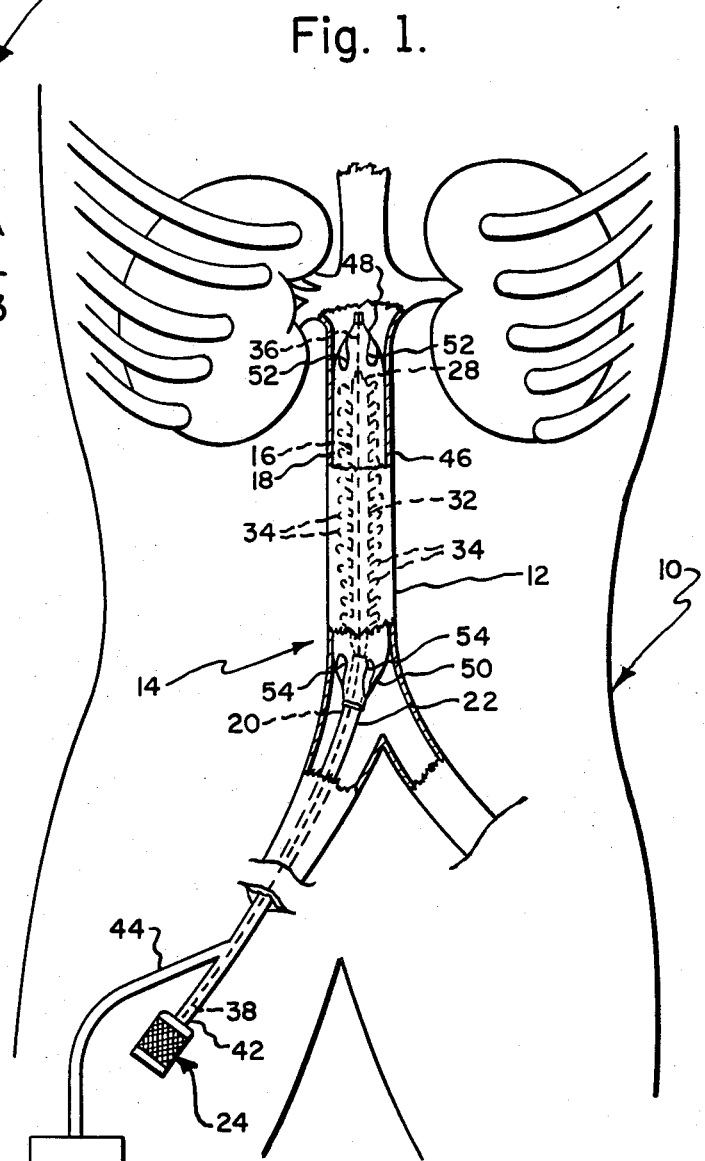
FIG. 1 is a somewhat schematic view illustrating the manner in which the oxygenator of this invention is used in a patient.
Figure 2:
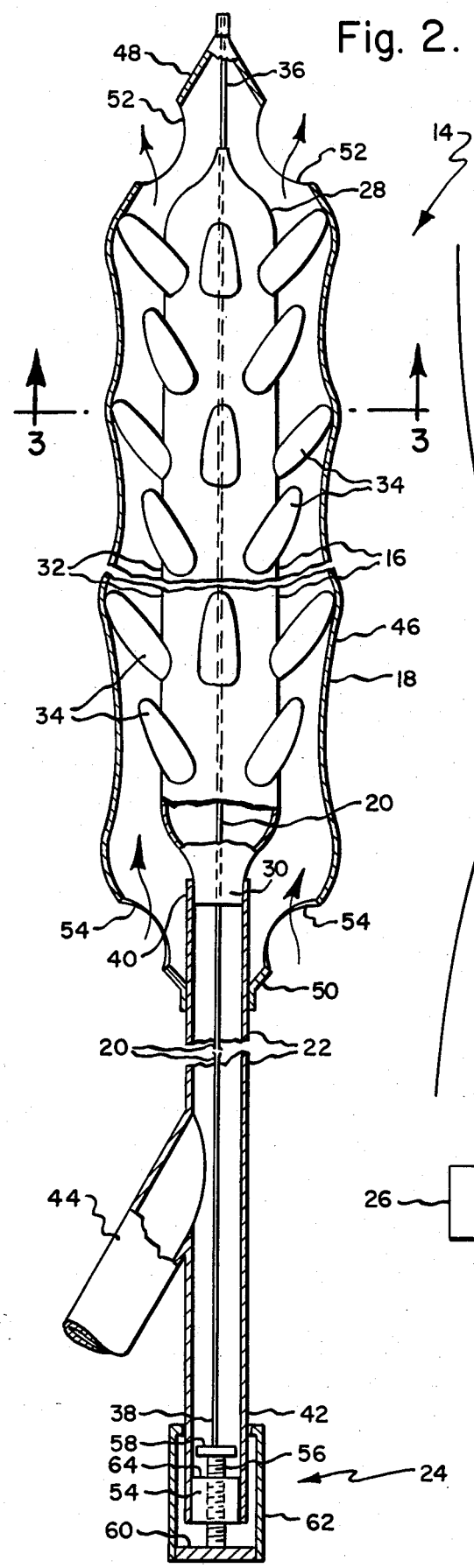
FIG. 2 is an enlarged view of the oxygenator shown in FIG. 1, portions being broken away and shown in section for purposes of clarity.
Figure 3:
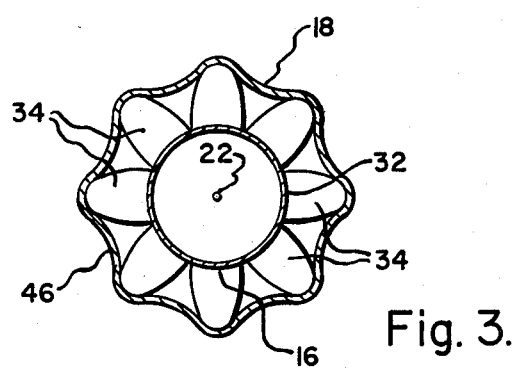
FIG. 3 is a section taken generally along the line 3—3 in FIG. 2.

Referring first to FIG. 1, a patient is shown somewhat schematically at 10, the patient's inferior vena cava being indicated at 12. A very substantial volume of blood customarily flows through the inferior vena cava which blood, being venous blood, can readily absorb oxygen. (The carbon dioxide is diffused within the blood and will be expelled through the patient's lungs.) The oxygenator, which is indicated generally at 14, is inserted percutaneously, and devices are available for percutaneous insertion of the oxygenator.

The major components of the oxygenator are a hollow membrane 16, a sheath 18 which is disposed about the hollow membrane 16, support wire means 20 for supporting the hollow membrane and sheath, tubular means 22 through which oxygen can be introduced into the hollow membrane, rotatable means 24 for rotating the support wire means 20 relative to the tubular means 22, and an oxygen supply and pressure regulator 26.

The hollow membrane 16 is formed of a gas permeable material, such as microporous polypropylene having a one mil thickness, and is closed at one end 28, the other end 30 of the membrane being bonded to one end 40 of the tubular means 22 in such a manner that oxygen can be introduced to the interior of the hollow membrane 16. When the hollow membrane is inflated, as when filled with oxygen under pressure, it can be seen that it has an elongated central tube 32 and a plurality of outwardly extending diffusion elements 34. The central tube 32 and diffusion elements 34 resemble a small branch of a pine tree provided with pine needles. The function of the diffusion elements is to increase the overall surface area of the hollow membrane 16 and thus it should be obvious that other forms of structure may be employed to increase the surface of the hollow membrane. However, such other forms should not restrict the flow of the blood through the associated blood vessel. In this regard it should be observed that while the overall inflated diameter of the hollow tube with pine needles is approximately the diameter of the blood vessel into which it is to be inserted, for example approximately 2 cm, the diameter of the central tube is only approximately 1 cm, thus leaving an unblocked cross-sectional area of approximately 75%. Therefore, the oxygenator does not materially restrict the flow of blood through the associated blood vessel.

The support means 20 for supporting the hollow membrane 16 is a wire made of a spring steel suitable for use in surgical procedures. The wire will normally have a linear set but can be flexed for purposes of insertion. Additionally, the wire 20 will have relatively high torsional resistance. The closed end 28 of the hollow membrane 16 is bonded in an airtight manner to one end 36 of the wire 20 for rotation therewith. (The other end 38 of the wire 20 is secured to the rotatable means 24 in a manner which will be more fully brought out below.)

The tubular means 22 consists of a somewhat flexible plastic tube which is disposed about the wire 20, one end 40 of the tube having the other end 30 of the membrane bonded thereto in such a manner that the end of the membrane cannot rotate relative to the end of the tube. Disposed between the one end 40 and the other end 42 is a Y section having a branch tube 44 which extends to the oxygen supply and pressure regulator 26. (The other end 42 of the tube is interconnected with the rotatable means 24 in a manner which will be more fully brought out below.)

The sheath 18 is formed from a flexible elastic material such as the type utilized in cardiovascular ballons. The sheath has a main cylindrical portion 46 and apertured end portions 48 and 50, the apertures being indicated generally by the reference numeral 52. The apex of the end portion 48 is bonded to the end 36 of the wire 20 for rotation with the wire. The apex of the other end 50 of the sheath 18 is bonded about the end 40 of the tube 22 in such a manner that it will not rotate relative to the tube.

The oxygen supply and regulating means is not shown in detail. However, it should be appreciated that in many situations the oxygen supply will be that available in a hospital room from a source within a hospital. While the regulated pressure of oxygen to be received within the hollow membrane 16 should be in the neighborhood of four pounds per square inch, it is desired that the membrane be flexed during operation to increase the turbulence of the blood flow across the surface of the membrane thereby increasing the transfer of oxygen from one side of the membrane to the other. This can be accomplished merely by pulsing the flow of oxygen into the membrane. Various means can be utilized for this purpose and one such means could be, for example, a relatively resilient balloon shaped member which, in its normal configuration, is generally spherical, which spherical resilient element can be mechanically compressed to expel oxygen from the spherical element into the membrane, and when released will tend to deflate the membrane. Obviously, other forms of pressure regulating devices can be utilized which will insure proper flow of oxygen into the system and will also insure proper transfer of oxygen from one side of the membrane to the blood on the other side of the membrane.

The rotatable means 24 is used to facilitate the insertion of the oxygenator into the patient's body. In this respect it should be appreciated that it is desirable that the device be inserted initially through a relatively small diameter blood vessel before it is received within a major blood vessel, such as the inferior vena cava. In order to insure that the overall diameter of the hollow membrane and sheath are reduced, the support member or wire 20 is rotated relative to the tubular portion 22 which will cause the hollow membrane and sheath to be twisted and wrapped upon the wire to a relatively small diameter. Accordingly, the other end of the tube 42 is non-rotatably secured to a threaded sleeve 54. Similarly, the other end of the wire 38 is non-rotatably secured to a threaded rod-like element 56 which is rotatably received within the sleeve 54. The rod-like element is provided with fixed inner and outer stops 58,60, respectively, which are adapted to abut against ends of the sleeve 54 to limit rotation of the rod-like element 56 relative thereto. A turning element 62 has one end fixed to stop 60, the turning element extending over the sleeve 54 and the end 42 of the tube. As the end 42 of the tube is fixed relative to the sleeve 54, and as the end 38 of the wire 20 is fixed relative to the threaded rod-like element 56, and as the stop 60 is both fixed to the rod-like element 56 and the turning element 62, it can be seen that when the turning element 62 is rotated with respect to the end 42 of the tube 22, that the wire 20 will be rotated with respect to the tube 22 causing the ends 28 and 48 of the hollow membrane 16 and sheath 18 to rotate with respect to their other ends 30, 50. For example, if the membrane and sheath are not twisted when the stop 58 bears against the surface 64 of the sleeve 54, corresponding rotational movement of the turning element 62 relative to the tube will then cause the sheath and hollow membrane to twist about the wire support 20, this operation being performed during the insertion of the oxygenator into the patient's body. After the parts have been positioned in their proper location, the rotatable element 62 is then turned in the other direction with respect to the tube 22 until the stop 58 again contacts the surface 64 at which point the hollow membrane and sheath will no longer be twisted about the wire. After the rotatable element 62 has been returned to its initial position where the membrane 16 and sheath 18 are not twisted about the wire 20, then the oxygen supply system 26 is connected to the wide tube 44 to introduce oxygen into the membrane in a manner which has been more fully set forth above.

While a preferred structure in which the principles of the present invention have been incorporated as shown and described above, it is to be understood that this invention is not to be limited to the particular details shown and described above, but that, in fact, widely differing means may be employed in the broader aspects of this invention.

What is claimed is:

1. An oxygenator capable of oxygenating blood within a patient's body comprising:
    an elongated wire support of such length that one end portion of the support may be disposed within a patient's body at the location where blood is to be oxygenated with the other end portion of the support being disposed outside the patient's body;
    an elongated hollow membrane formed of a gas permeable material and capable of being twisted to a collapsed condition, said membrane being closed at one end and open at the other end, the closed end being secured to said one end portion of said wire, said wire supporting said hollow membrane during insertion into a patient's body, said membrane being fully inserted within the patient's body during oxygenation; and tubular means having one end portion connected to the open end of said hollow membrane, and other end portion connectible to an oxygen supply when the hollow membrane is disposed within the patient's body whereby oxygen may be introduced into said membrane through said tubular means, a portion of said wire support passing through said tubular means.

2. The oxygenator as set forth in claim 1 further characterized by the provision of pressure regulating means, said pressure regulating means being capable of varying the oxygen pressure within the hollow membrane in a manner suitable for maximum oxygen transfer and blood flow.

3. The oxygenator as set forth in claim 1 wherein the hollow membrane is provided with an irregular surface to increase the surface area in contact with the blood whereby oxygen transfer between the membrane and the blood can be increased.

4. The oxygenator as set forth in claim 1 further characterized by the provision of an elongated hollow sheath disposed about said hollow membrane and capable of being twisted to a collapsed condition about said wire and said hollow membrane, one end of the sheath being secured to said one end portion of said wire support and the other end of said sheath being connected to said one end portion of said tubular means, said sheath facilitating the insertion of the hollow membrane into the body, and wherein said sheath is provided with suitable apertures adjacent each end whereby the blood can flow through the sheath after insertion.

5. The oxygenator as set forth in claim 4 wherein the hollow membrane is provided with an irregular surface to increase the surface area in contact with the blood whereby oxygen transfer between the membrane and the blood can be increased, said irregular surface also supporting said sheath after insertion.

6. The oxygenator as set forth in claim 4 further characterized by the provision of rotatable means journaled about the other end of said tubular means and connected to said wire support, said rotatable means being capable of causing said wire support to be rotated relative to said tubular means to cause said membrane and sheath to be twisted to their collapsed condition during insertion into a patient's body and to be untwisted after insertion for maximum oxygenation of the blood.

7. The oxygenator as set forth in claim 1 further characterized by the provision of rotatably means journaled about the other end of said tubular means and connected to said wire support and capable of causing the wire support to be rotated relative to said tubular means whereby the membrane can be twisted to its collapsed condition during insertion into a patient's body, and can be untwisted after insertion for maximum oxygenation of the blood.

8. An oxygenator capable of oxygenating blood within a patient's body comprising:

an elongated wire support having one end portion disposed within a patient's body during oxygenation, and the other end being disposed outside of said body;

an elongated hollow membrane formed of a gas permeable material and capable of being twisted to a collapsed condition during insertion into said body, said membrane being disposed entirely within said body during oxygenation, said membrane being closed at one end and open at the other end, the closed end being supported on said one end portion of said wire, said membrane being provided with a plurality of radially outwardly extending diffusion elements;

elongated tubular means having one end portion connected to the open end of said hollow membrane, and another end connectible to an oxygen supply when the hollow membrane is disposed within a patient's body whereby oxygen may be introduced into said membrane through said tubular means;

an elongated hollow sheath capable of being twisted to a collapsed condition, said sheath being disposed about said hollow membrane, one end of the sheath being secured to said one end portion of said wire support and the other end being connected to said one end portion of the tubular means, said sheath facilitating the insertion of the hollow membrane into said body, and said sheath being disposed entirely within said body during oxygenation, said sheath further being provided with suitable apertures adjacent each end whereby blood can flow through the sheath during oxygenation, said sheath being supported in part by said plurality of radially outwardly extending diffusion elements during oxygenation; and rotatable means journaled about said another end of the tubular means and capable of causing said wire support to be rotated relative to the tubular means whereby said membrane and said sheath can be twisted to their collapsed condition during insertion and can be untwisted after insertion for maximum oxygenation of the blood.

9. A method of oxygenating the blood within a patient comprising the following steps:

providing an elongated hollow gas permeable membrane;

providing an elongated wire support means which is capable of being inserted into a blood vessel of a patient;

twisting the hollow gas permeable membrane about said elongated wire support means;

inserting said hollow membrane and the elongated wire support means into a blood vessel which normally contains deoxygenated blood;

untwisting the gas permeable membrane; and introducing oxygen under pressure into said hollow membrane when it is disposed within said blood vessel to cause oxygen to pass through the gas permeable membrane into the blood thereby increasing the oxygen content of the blood.

10. The method as set forth in claim 9 further characterized by the steps of, providing a sheath disposable about said elongated wire support means and said hollow membrane; and simultaneously twisting and untwisting the wire support means, the sheath and the hollow membrane.

* * * * *